United States Patent
Matoba et al.

(10) Patent No.: US 9,062,010 B2
(45) Date of Patent: Jun. 23, 2015

(54) CRYSTALLINE POLYMORPHS OF ISOXAZOLINE COMPOUND AND PRODUCTION METHOD THEREOF

(71) Applicant: NISSAN CHEMICAL INDUSTRIES, LTD., Tokyo (JP)

(72) Inventors: Kazutaka Matoba, Funabashi (JP); Takeshi Mita, Funabashi (JP); Kotatsu Matsubara, Funabashi (JP); Takahiro Kagami, Shiraoka (JP); Kunimitsu Nakahira, Shiraoka (JP); Masaki Kobayashi, Shiraoka (JP); Hotaka Imanaka, Shiraoka (JP); Rika Miyachi, Funabashi (JP); Masashi Ohno, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 14/317,484

(22) Filed: Jun. 27, 2014

(65) Prior Publication Data
US 2015/0005507 A1    Jan. 1, 2015

(30) Foreign Application Priority Data

Jun. 27, 2013  (JP) .................. 2013-134847

(51) Int. Cl.
*C07D 261/04*    (2006.01)
(52) U.S. Cl.
CPC .................. *C07D 261/04* (2013.01)

(58) Field of Classification Search
None
See application file for complete search history.

(56) References Cited

U.S. PATENT DOCUMENTS

| | | | |
|---|---|---|---|
| 8,022,089 B2 * | 9/2011 | Mita et al. ............. | 514/378 |
| 8,492,311 B2 * | 7/2013 | Mita et al. ............. | 504/271 |
| 8,796,464 B2 * | 8/2014 | Moriyama et al. ...... | 548/240 |
| 2007/0066617 A1 | 3/2007 | Mita et al. | |
| 2013/0144066 A1 | 6/2013 | Kousaka et al. | |

FOREIGN PATENT DOCUMENTS

| | | |
|---|---|---|
| JP | A-2007-308471 | 11/2007 |
| JP | A-2011-51977 | 3/2011 |
| WO | WO 2005/085216 A1 | 9/2005 |
| WO | WO 2009/063910 A1 | 5/2009 |
| WO | WO 2010/005048 A1 | 1/2010 |
| WO | WO 2013/069731 A1 | 5/2013 |

OTHER PUBLICATIONS

Office Action issued in U.S. Appl. No. 13/757,045 dated Nov. 18, 2013.

* cited by examiner

*Primary Examiner* — Kamal Saeed
(74) *Attorney, Agent, or Firm* — Oliff PLC

(57) ABSTRACT

A method for manufacturing a crystal and a crystal of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide and a method for manufacturing the crystal. It is elucidated that (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has a crystalline polymorph.

12 Claims, 3 Drawing Sheets

CRYSTALLINE POLYMORPHS OF ISOXAZOLINE COMPOUND AND PRODUCTION METHOD THEREOF

TECHNICAL FIELD

The present invention relates to a crystalline polymorph related to the optically active substance of 4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide (hereinafter referred to as Compound A), and a production method of the crystalline polymorph.

BACKGROUND ART

When chemical compounds are in solid states, they can be either amorphous (that is, long-distance order does not exist in positions of atoms) or crystalline (that is, atoms are aligned with ordered repetitive patterns). Although in most cases, only a single crystalline form has been known for each of the compounds when they are in solid states, polymorphs have also been found in some compounds. The term "polymorph" refers to a specific crystalline form of a chemical compound that can take two or more crystalline forms (that is, a crystal lattice structure) in solid states.

On the other hand, the Compound A that is included in the present invention has already been known to be useful as a pest control chemical (see, for example, Patent Document 1). In the present invention, the pest control chemical refers to a chemical for exterminating harmful arthropods in the fields of agriculture and horticulture or of animal husbandry and hygiene (a chemical for exterminating endoparasites or ectoparasites, which are found in mammals or birds as domestic animals or pets; or a chemical for exterminating sanitary insects and unpleasant insects for household or business uses). In addition, a method for manufacturing the optically active substance of the Compound A has also been known already (see, for example, Patent Documents 1, 2, and 3).

Also, a crystalline polymorph related to the racemate of the Compound A (see, for example, Patent Document 4), and an amorphous material related to the optically active substance of the Compound A, which comes from an asymmetric carbon at position 5 of an isoxazoline ring have already been known (see, for example, Patent Document 1).

PRIOR ART DOCUMENTS

Patent Documents

Patent Document 1: WO 2005/085216
Patent Document 2: WO 2009/063910
Patent Document 3: Japanese Patent Application Publication No. 2011-051977 (JP 2011-051977 A)
Patent Document 4: WO 2010/005048

SUMMARY OF THE INVENTION

Problem to be Solved by the Invention

Even today, it is still impossible to predict physical characteristics, such as melting points and water solubility for crystals of chemical compounds. Moreover, it is also impossible to predict if a compound in a solid state can take two or more crystalline forms, that is, to predict if the crystalline form includes crystalline polymorphs.

It is an object of the present invention to provide a novel crystal related to the optically active substance of the Compound A, and a method for manufacturing the crystal.

Means for Solving the Problem

As a result of intensive study, the inventors of the present invention have found a novel crystalline polymorph related to the optically active substance of the Compound A.

Specifically, the present invention relates to [1] to [12] below.

[1]
A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=6.56, 7.38, 11.52, 12.92, 13.19, 15.60, 16.04, 16.36, 17.59, 18.27, 18.47, 19.45, 20.62, 21.12, 22.20, 23.19, 24.59, 25.12, 25.74, and 26.48 in powder X-ray diffraction with a Cu—Kα ray.

[2]
The crystalline polymorph according to [1], in which characteristic peaks are at angles of diffraction 2θ=3.66, 5.73, 6.56, 7.38, 7.76, 9.18, 11.52, 12.24, 12.92, 13.19, 13.98, 14.81, 15.60, 16.04, 16.36, 16.98, 17.59, 18.02, 18.27, 18.47, 18.87, 19.45, 20.21, 20.48, 20.62, 21.12, 21.51, 21.92, 22.20, 22.66, 23.19, 23.58, 24.24, 24.59, 24.96, 25.12, 25.74, 26.08, 26.48, 27.52, 28.20, 29.18, 29.61, 30.06, 30.50, 30.88, 35.77, and 38.92 in powder X-ray diffraction with a Cu—Kα ray.

[3]
A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=6.56±0.2, 7.38±0.2, 11.52±0.2, 12.92±0.2, 13.19±0.2, 15.60±0.2, 16.04±0.2, 16.36±0.2, 17.59±0.2, 18.27±0.2, 18.47±0.2, 19.45±0.2, 20.62±0.2, 21.12±0.2, 22.20±0.2, 23.19±0.2, 24.59±0.2, 25.12±0.2, 25.74±0.2, and 26.48±0.2 in powder X-ray diffraction with a Cu—Kα ray.

[4]
The crystalline polymorph according to [3], in which characteristic peaks are at angles of diffraction 2θ=3.66±0.2, 5.73±0.2, 6.56±0.2, 7.38±0.2, 7.76±0.2, 9.18±0.2, 11.52±0.2, 12.24±0.2, 12.92±0.2, 13.19±0.2, 13.98±0.2, 14.81±0.2, 15.60±0.2, 16.04±0.2, 16.36±0.2, 16.98±0.2, 17.59±0.2, 18.02±0.2, 18.27±0.2, 18.47±0.2, 18.87±0.2, 19.45±0.2, 20.21±0.2, 20.48±0.2, 20.62±0.2, 21.12±0.2, 21.51±0.2, 21.92±0.2, 22.20±0.2, 22.66±0.2, 23.19±0.2, 23.58±0.2, 24.24±0.2, 24.59±0.2, 24.96±0.2, 25.12±0.2, 25.74±0.2, 26.08±0.2, 26.48±0.2, 27.52±0.2, 28.20±0.2, 29.18±0.2, 29.61±0.2, 30.06±0.2, 30.50±0.2, 30.88±0.2, 35.77±0.2, and 38.92±0.2 in powder X-ray diffraction with a Cu—Kα ray.

[5]
The crystalline polymorph according to any one of [1] to [4], in which a diffraction curve of the crystalline polymorph is substantially identical to a diffraction curve shown in FIG. 1 of the present application in powder X-ray diffraction with a Cu—Kα ray.

[6]
The crystalline polymorph according to any one of [1] to [5], in which the crystalline polymorph is obtained by dissolving (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide in toluene, and then precipitating a crystal.

[7]

A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=3.46, 4.48, 7.12, 8.69, 8.92, 10.50, 11.07, 11.94, 12.49, 12.94, 14.49, 15.22, 15.62, 16.26, 16.64, 17.27, 17.96, 19.20, 20.04, 20.62, 21.08, 22.36, 22.68, 23.02, 23.82, 24.96, 25.65, 26.46, 27.09, 27.67, 28.57, 29.18, 30.01, 30.78, 31.34, 32.14, 33.79, 35.85, and 37.57 in powder X-ray diffraction with a Cu—Kα ray.

[8]

A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=3.46±0.2, 4.48±0.2, 7.12±0.2, 8.69±0.2, 8.92±0.2, 10.50±0.2, 11.07±0.2, 11.94±0.2, 12.49±0.2, 12.94±0.2, 14.49±0.2, 15.22±0.2, 15.62±0.2, 16.26±0.2, 16.64±0.2, 17.27±0.2, 17.96±0.2, 19.20±0.2, 20.04±0.2, 20.62±0.2, 21.08±0.2, 22.36±0.2, 22.68±0.2, 23.02±0.2, 23.82±0.2, 24.96±0.2, 25.65±0.2, 26.46±0.2, 27.09±0.2, 27.67±0.2, 28.57±0.2, 29.18±0.2, 30.01±0.2, 30.78±0.2, 31.34±0.2, 32.14±0.2, 33.79±0.2, 35.85±0.2, and 37.57±0.2 in powder X-ray diffraction with a Cu—Kα ray.

[9]

The crystalline polymorph according to [7] or [8], in which a diffraction curve of the crystalline polymorph is substantially identical to a diffraction curve shown in FIG. 5 of the present application in powder X-ray diffraction with a Cu—Kα ray.

[10]

The crystalline polymorph according to any one of [7] to [9], in which the crystalline polymorph is obtained by dissolving (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide in ethanol, and then precipitating a crystal.

[11]

A composition for pest control, comprising the crystalline polymorph as described in any one of [1] to [6].

[12]

A composition for pest control, comprising the crystalline polymorph as described in any one of [7] to [10].

Effects of the Invention

According to the present invention, a crystalline polymorph related to the optically active substance of the Compound A can be controlled. Also, the obtained crystalline polymorph related to the optically active substance of the Compound A has excellent physical characteristics, such as hygroscopicity and stability in formulations; and physiological characteristics, such as insecticidal activity and bioavailability.

MODES FOR CARRYING OUT THE INVENTION

Figure 1:
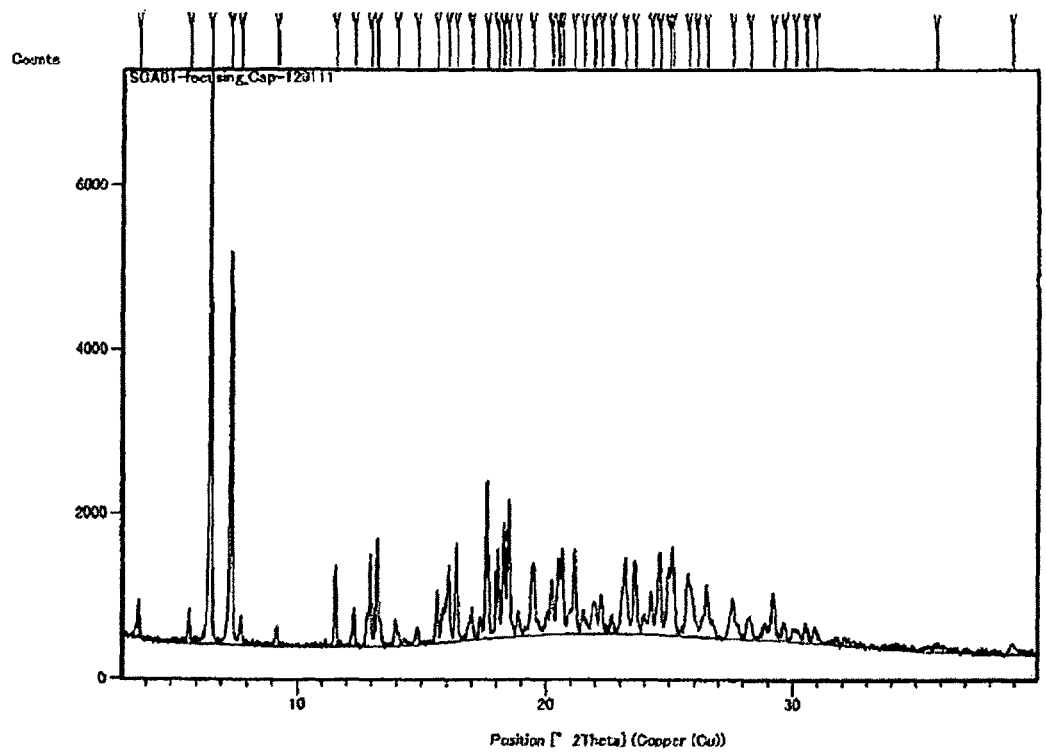
FIG. 1 is a chart of powder X-ray diffraction for the crystalline polymorph of the (S)-Compound A obtained in Example 1-1.

The Compound A is 4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide.

The Compound A in this specification has optically active substances that come from the asymmetric carbon at position 5 of the isoxazoline ring, and the optically active substance is the S-isomer. An optical purity of the optically active substance is 80 to 100% ee, preferably 90 to 100% ee, more preferably 93.0 to 100% ee, still more preferably 94.0 to 100% ee, and most preferably 97.0 to 99.9% ee.

Note that the S-isomer of the optically active substance of the Compound A is depicted as "(S)-Compound A" in this specification.

The characteristics of a crystalline polymorph of the (S)-Compound A will be explained in detail in the following (1) and (2).

(1) The crystalline polymorph that is obtained by dissolving the (S)-Compound A in an aromatic hydrocarbon solvent, such as toluene, and then precipitating a crystal, has peaks at angles of diffraction (2θ) of 3.66, 5.73, 6.56, 7.38, 7.76, 9.18, 11.52, 12.24, 12.92, 13.19, 13.98, 14.81, 15.60, 16.04, 16.36, 16.98, 17.59, 18.02, 18.27, 18.47, 18.87, 19.45, 20.21, 20.48, 20.62, 21.12, 21.51, 21.92, 22.20, 22.66, 23.19, 23.58, 24.24, 24.59, 24.96, 25.12, 25.74, 26.08, 26.48, 27.52, 28.20, 29.18, 29.61, 30.06, 30.50, 30.88, 35.77, and 38.92 in a powder X-ray diffraction spectrum. The peak values above are those of the crystalline polymorph obtained according to the method described in Example 1-1 below, and the chart of the powder X-ray diffraction spectrum thereof is shown in FIG. 1.

An error of a peak of powder X-ray diffraction may usually be ±0.2, or may possibly be ±0.1, and thus the peak values of a crystalline polymorph by considering errors are usually 2θ=3.66±0.2, 5.73±0.2, 6.56±0.2, 7.38±0.2, 7.76±0.2, 9.18±0.2, 11.52±0.2, 12.24±0.2, 12.92±0.2, 13.19±0.2, 13.98±0.2, 14.81±0.2, 15.60±0.2, 16.04±0.2, 16.36±0.2, 16.98±0.2, 17.59±0.2, 18.02±0.2, 18.27±0.2, 18.47±0.2, 18.87±0.2, 19.45±0.2, 20.21±0.2, 20.48±0.2, 20.62±0.2, 21.12±0.2, 21.51±0.2, 21.92±0.2, 22.20±0.2, 22.66±0.2, 23.19±0.2, 23.58±0.2, 24.24±0.2, 24.59±0.2, 24.96±0.2, 25.12±0.2, 25.74±0.2, 26.08±0.2, 26.48±0.2, 27.52±0.2, 28.20±0.2, 29.18±0.2, 29.61±0.2, 30.06±0.2, 30.50±0.2, 30.88±0.2, 35.77±0.2, and 38.92±0.2; and are possibly 2θ=3.66±0.1, 5.73±0.1, 6.56±0.1, 7.38±0.1, 7.76±0.1, 9.18±0.1, 11.52±0.1, 12.24±0.1, 12.92±0.1, 13.19±0.1, 13.98±0.1, 14.81±0.1, 15.60±0.1, 16.04±0.1, 16.36±0.1, 16.98±0.1, 17.59±0.1, 18.02±0.1, 18.27±0.1, 18.47±0.1, 18.87±0.1, 19.45±0.1, 20.21±0.1, 20.48±0.1, 20.62±0.1, 21.12±0.1, 21.51±0.1, 21.92±0.1, 22.20±0.1, 22.66±0.1, 23.19±0.1, 23.58±0.1, 24.24±0.1, 24.59±0.1, 24.96±0.1, 25.12±0.1, 25.74±0.1, 26.08±0.1, 26.48±0.1, 27.52±0.1, 28.20±0.1, 29.18±0.1, 29.61±0.1, 30.06±0.1, 30.50±0.1, 30.88±0.1, 35.77±0.1, and 38.92±0.1.

[Analytical Conditions of Powder X-ray Diffraction]

Device: X'pert Pro MPD (manufactured by PANalytical B.V.)

X-ray source: Cu

Voltage: 45 kV

Current: 40 mA

Data range: 3.0066 to 39.9916 deg
Scan axis: 2θ only
Step size: 0.0130 deg
Scan step time: 24.6440 sec
Type of scan: Continuous
PSD mode: Scanning
PSD distance: 0.80 deg
Divergence slit: 0.4354 deg
Sample width: 10.00 mm
Measurement temperature: 25.00° C.
Radius of goniometer: 240.00 mm
Distance between focus and DS: 100.00 mm Any types of the (S)-Compound A can be used as raw materials for crystallization or phase transition. For example, the (S)-Compound A can be a crystalline polymorph including a pseudopolymorph; an amorphous material; a mixture thereof; or a solution.

As a solvent, an aromatic hydrocarbon solvent, such as benzene, toluene, xylene, chlorobenzene, o-dichlorobenzene, m-dichlorobenzene, p-dichlorobenzene, nitrobenzene, and tetrahydronaphthalene can be used. Among these solvents, toluene is particularly preferable.

In a method for manufacturing a crystalline polymorph of the (S)-Compound A, the (S)-Compound A is dissolved in a solvent, the amount of which is as small as possible, for example, an amount that allows supersaturation; and the obtained solution is rested in an open system or a closed system so that the (S)-Compound A can be crystallized.

A temperature for dissolving the (S)-Compound A in a solvent is usually 0 to 100° C. A rate of cooling is usually 0.1 to 20° C./hour. A resting time is usually one minute or more.

The crystalline polymorph of the (S)-Compound A obtained by the method described above may contain the solvent used.

Figure 5:
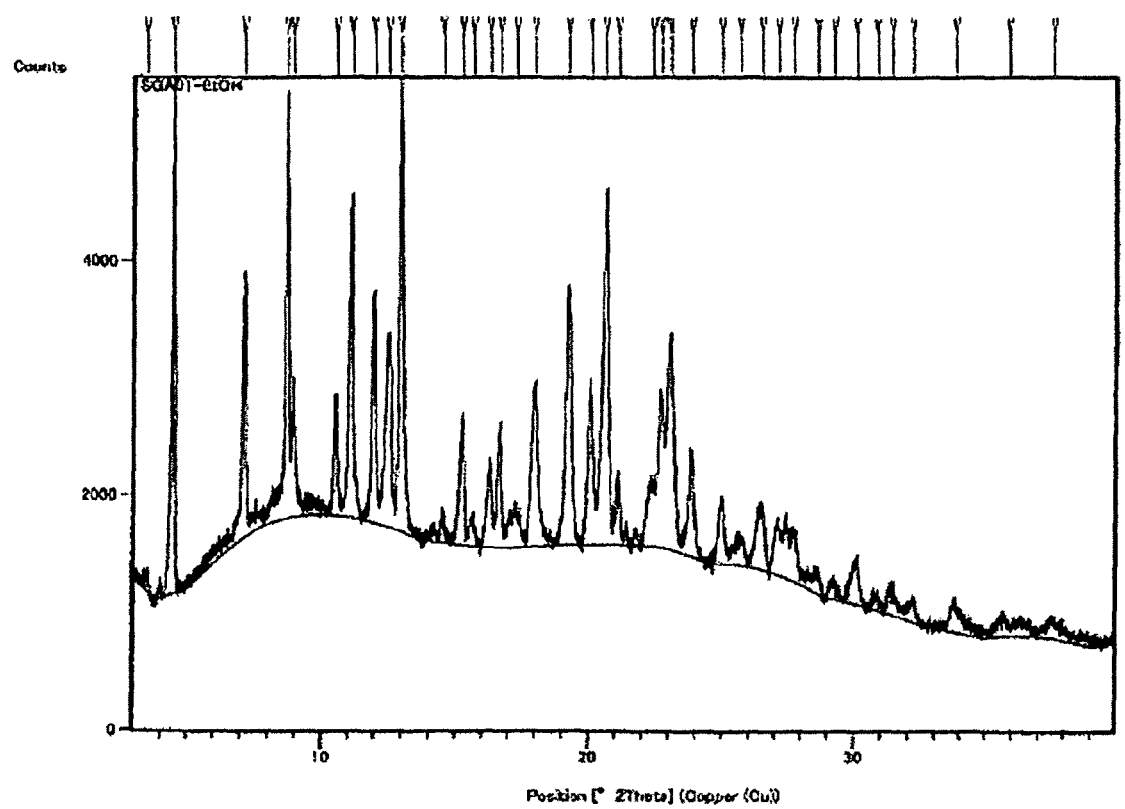
FIG. 5 is a chart of powder X-ray diffraction for the crystalline polymorph of the (S)-Compound A obtained in Example 3.

(2) The crystalline polymorph that is obtained by dissolving the (S)-Compound A in an alcohol solvent, such as ethanol, and then precipitating a crystal, has peaks at angles of diffraction (2θ) of 3.46, 4.48, 7.12, 8.69, 8.92, 10.50, 11.07, 11.94, 12.49, 12.94, 14.49, 15.22, 15.62, 16.26, 16.64, 17.27, 17.96, 19.20, 20.04, 20.62, 21.08, 22.36, 22.68, 23.02, 23.82, 24.96, 25.65, 26.46, 27.09, 27.67, 28.57, 29.18, 30.01, 30.78, 31.34, 32.14, 33.79, 35.85, and 37.57 in a powder X-ray diffraction spectrum. The peak values of above were obtained in Example 3 below, and the chart of the powder X-ray diffraction spectrum thereof is shown in FIG. 5.

An error of a peak of powder X-ray diffraction may usually be ±0.2, or may possibly be ±0.1, and thus the peak values of a crystalline polymorph by considering errors are usually 2θ=3.46±0.2, 4.48±0.2, 7.12±0.2, 8.69±0.2, 8.92±0.2, 10.50±0.2, 11.07±0.2, 11.94±0.2, 12.49±0.2, 12.94±0.2, 14.49±0.2, 15.22±0.2, 15.62±0.2, 16.26±0.2, 16.64±0.2, 17.27±0.2, 17.96±0.2, 19.20±0.2, 20.04±0.2, 20.62±0.2, 21.08±0.2, 22.36±0.2, 22.68±0.2, 23.02±0.2, 23.82±0.2, 24.96±0.2, 25.65±0.2, 26.46±0.2, 27.09±0.2, 27.67±0.2, 28.57±0.2, 29.18±0.2, 30.01±0.2, 30.78±0.2, 31.34±0.2, 32.14±0.2, 33.79±0.2, 35.85±0.2, and 37.57±0.2; and are possibly 2θ=3.46±0.1, 4.48±0.1, 7.12±0.1, 8.69±0.1, 8.92±0.1, 10.50±0.1, 11.07±0.1, 11.94±0.1, 12.49±0.1, 12.94±0.1, 14.49±0.1, 15.22±0.1, 15.62±0.1, 16.26±0.1, 16.64±0.1, 17.27±0.1, 17.96±0.1, 19.20±0.1, 20.04±0.1, 20.62±0.1, 21.08±0.1, 22.36±0.1, 22.68±0.1, 23.02±0.1, 23.82±0.1, 24.96±0.1, 25.65±0.1, 26.46±0.1, 27.09±0.1, 27.67±0.1, 28.57±0.1, 29.18±0.1, 30.01±0.1, 30.78±0.1, 31.34±0.1, 32.14±0.1, 33.79±0.1, 35.85±0.1, and 37.57±0.1.

[Analytical Conditions of Powder X-ray Diffraction]
Device: X'pert Pro MPD (manufactured by PANalytical B.V.)
X-ray source: Cu
Voltage: 45 kV
Current: 40 mA
Data range: 3.0066 to 39.9916 deg
Scan axis: 2θ only
Step size: 0.0130 deg
Scan step time: 24.6440 sec
Type of scan: Continuous
PSD mode: Scanning
PSD distance: 0.80 deg
Divergence slit: 0.4354 deg
Sample width: 10.00 mm
Measurement temperature: 25.00° C.
Radius of goniometer: 240.00 mm
Distance between focus and DS: 100.00 mm Any types of the (S)-Compound A can be used as raw materials for crystallization or phase transition. For example, the (S)-Compound A can be a crystalline polymorph including a pseudopolymorph; an amorphous material; a mixture thereof; or a solution.

As a solvent, an alcohol solvent, such as methanol, ethanol, 1-propanol, 2-propanol, 1-butanol, 2-butanol, isobutanol, 2-methyl-2-propanol, methyl cellosolve, ethyl cellosolve, i-propyl cellosolve, diethylene glycol monomethyl ether, diethylene glycol monoethyl ether, diethylene glycol mono butyl ether, cyclohexanol, and benzyl alcohol can be used. Among these solvents, ethanol is particularly preferable.

In a method for manufacturing a crystalline polymorph of the (S)-Compound A, the (S)-Compound A is dissolved in a solvent, the amount of which is as small as possible, for example, an amount that allows supersaturation; and the obtained solution is rested in an open system or a closed system so that the (S)-Compound A can be crystallized.

A temperature for dissolving the (S)-Compound A in a solvent is usually 0 to 100° C. A rate of cooling is usually 0.1 to 20° C./hour. A resting time is usually one minute or more.

The crystalline polymorph of the (S)-Compound A obtained by the method described above may contain the solvent used.

Properties, such as specific gravity, solubility, hygroscopicity, photodegradability, surface energy, lipid solubility, biological membrane permeability, absorbability, stability, and effect persistency, of the crystalline polymorph of the optically active substance of the Compound A described in (1) or (2) above may be different from properties of the crystal of the racemate of the Compound A, or properties of the amorphous material of the optically active substance of the Compound A.

In addition to the crystalline polymorph of the (S)-Compound A, one or more of known agrichemicals, such as a herbicide, an insecticide, a miticide, a nematicide, an antiviral agent, a plant growth regulator, a microbicide, a synergist, an attractant, and a repellent can be added; or one or more of known veterinary drugs can further be added, and in such cases, a more superior pest control effect may be obtained. Particularly preferable known agrichemicals are a microbicide, a bactericide, a nematicide, a miticide, and an insecticide. Specific examples thereof will be listed below, but not limited thereto.

Microbicides: acibenzolar-S-methyl, acylaminobenzamide, acypetacs, aldimorph, ametoctradin, amisulbrom, amobam, ampropyfos, anilazine, azaconazole, azithiram, azoxystrobin, barium polysulfide, benalaxyl, benalaxyl-M, benodanil, benomyl, benquinox, bentaluron, benthiavalicarb, benthiazole, benzamacril, benzamorf, bethoxazine, binapacryl, biphenyl, bitertanol, blasticidin-S, bixafen, bordeaux mixture, boscalid, bromoconazole, bupirimate, buthiobate, calcium polysulfide, calcium polysulfide, captafol, captan, carpropamid, carbamorph, carbendazim, carboxin, carvone, cheshunt mixture, chinomethionat, chlobenthiazone, chloraniformethane, chloranil, chlorfenazol, chloroneb, chloropicrin, chlorothalonil, chlorquinox, chlozolinate, climbazole, clotrimazole, copper acetate, basic copper carbonate, copper hydroxide, copper naphthenate, copper oleate, copper oxychloride, copper sulfate, basic copper sulfate, copper zinc chromate, cufraneb, cuprobam, cyazofamid, cyclafuramid, cycloheximide, cyflufenamid, cymoxanil, cypendazole, cyproconazol, cyprodinil, cyprofuram, dazomet, debacarb, decafentin, dehydroacetic acid, dichlofluanid, dichlone, dichlorophen, dichlozoline, diclobutrazol, diclocymet, diclomedine, dicloran, and the like.

Microbicides (continued): diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipyrithione, ditalimfos, dithianon, dodemorph, dodine, drazoxolon, edifenphos, epoxiconazole, etaconazole, ethaboxam, etem, ethirimol, ethoxyquin, etridiazole, famoxadone, fenarimol, febuconazole, fenamidone, fenaminosulf, fenapanil, fendazosulam, fenfuram, fenhexamid, fenitropan, fenoxanil, fenpiclonil, fenpropidin, fenpyrazamine, fenpropimorph, fentin, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetyl-aluminium, fuberidazole, furalaxyl, furametpyr, furcarbanil, furconazole, furconazole-cis, furmecyclox, furphanate, glyodin, griseofulvin, guazatine, halacrinate, hexachlorobenzene, hexaconazole, hexylthiofos, 8-hydroxyquinoline sulfate, hymexazol, imazalil, imibenconazole, iminoctadine, ipconazole, iprobenfos, iprodione, iprovalicarb, isoprothiolane, isovaledione, and the like.

Microbicides (continued): kasugamycin, kresoxim-methyl, mancopper, mancozeb, mandipropamid, maneb, mebenil, mecarbinzid, mepanipyrim, mepronil, metalaxyl, metalaxyl-M, metam, metazoxolon, metconazole, methasulfocarb, methfuroxam, methyl isothiocyanate, metiram, metominostrobin, metrafenone, metsulfovax, milneb, myclobutanil, myclozolin, nabam, natamycin, nickel bis(dimethyldithiocarbamate), nitrostyrene, nitrothal-isopropyl, nuarimol, OCH, octhilinone, ofurace, orysastrobin, oxadixyl, oxine copper, oxycarboxin, oxpoconazole fumarate, pefurzoate, penconazole, penflufen, pencycuron, penthiopyrad, o-phenylphenol, phosdiphen, phthalide, picoxystrobin, piperalin, polycarbamate, polyoxins, polyoxorim, potassium azide, potassium hydrogen carbonate, proquinazid, probenazole, prochloraz, procymidone, propamocarb hydrochloride, propiconazole, propineb, prothiocarb, prothioconazole, pyracarbolid, pyraclostrobin, pyrazophos, pyridinitril, pyrifenox, pyrimethanil, pyriofenone, pyroquilon, pyroxychlor, pyroxyfur, quinomethionate, quinoxyfen, quintozene, quinacetolsulfate, quinazamid, quinconazole, rabenzazole, and the like.

Microbicides (continued): sodium azide, sodium hydrogen carbonate, sodium hypochlorite, sulfur, spiroxamine, salycylanilide, silthiofam, simeconazole, tebuconazole, tecnazene, tecoram, tetraconazole, thiabendazole, thiadifluor, thicyofen, thifluzamide, thiochlorfenphim, thiophanate, thiophanate-methyl, thioquinox, thiram, tiadinil, tioxymid, tolclofos-methyl, tolylfluanid, triadimefon, toriadimenol, triamiphos, triarimol, triazoxide, triazbutil, tributyltin oxide, trichlamide, tricyclazole, tridemorph, trifloxystrobin, triflumizole, trifo-rine, triticonazole, validamycin, valifenalate, vinclozolin, zarilamide, zinc sulfate, zineb, ziram, zoxamide, Chinese mushroom mycelium extract, and the like.

Bactericides: benzalkonium chloride, bithionol, bronopol, cresol, formaldehyde, nitrapyrin, oxolinic acid, oxyterracycline, streptomycin, tecloftalam, and the like.

Nematicides: aldoxycarb, cadusafos, DBCP, dichlofenthion, DSP, ethoprophos, fenamiphos, fensulfothion, fluensulfone, fosthiazate, fosthietan, imicyafos, isamidofos, isazofos, oxamyl, thionazin, and the like.

Miticides: acequinocyl, acrinathrin, amitraz, BCI-033 (test name), bifenazate, bromopropylate, chinomethionat, chlorobezilate, clofentezine, cyenopyrafen, cyflumetofen, cyhexatine, dicofol, dienochlor, DNOC, etoxazole, fenazaquin, fenbutatin oxide, fenothiocarb, fenpropathrin, fenpyroximate, fluacrypyrim, halfenprox, hexythiazox, milbemectin, propargite, pyridaben, pyrimidifen, S-1870 (test name), spirodiclofen, spyromesifen, NNI-0711 (test name), CL900167 (test name), tebufenpyrad, and the like.

Insecticides: abamectin, acephate, acetamipirid, alanycarb, aldicarb, allethrin, azamethiphos, azinphos-methyl, *bacillus thuringiensis*, bendiocarb, benfluthrin, benfuracarb, bensultap, bifenthrin, bioallethrin, bioresmethrin, bistrifluron, buprofezin, butocarboxim, carbaryl, carbofuran, carbosulfan, cartap, chlorantraniliprole, chlorethxyfos, chlorfenapyr, chlorfenvinphos, chlorfluazuron, chlormephos, chlorpyrifos, chlorpyrifos-methyl, chromafenozide, clothianidin, cyantraniliprole, cyclprothrin, cyflumetofen, cyfluthrin, beta-cyfluthrin, cyhalothrin, lambda-cyhalothrin, cypermethrin, alpha-cypermethrin, beta-cypermethrin, zeta-cypermethrin, cyromazine, deltamethrin, diacloden, diafenthiuron, diazinon, dichlorvos, diflubenzuron, dimethylvinphos, dinotefuran, diofenolan, disulfoton, dimethoate, emamectin-benzoate, empenthrin, endosulfan, alpha-endosulfan, EPN, esfenvalerate, ethiofencarb, ethiprole, etofenprox, etrimfos, fenitrothion, fenobucarb, fenoxycarb, fenpropathrin, fenthion, fenvalerate, fipronil, flonicamid, flubendiamide, flucythrinate, flufenerim, flufenoxuron, flufenprox, flumethrin, fluvalinate, tau-fluvalinate, fonophos, formetanate, formothion, furathiocarb, flufiprole, flupyradifurone, flometoquin, and the like.

Insecticides (continued): halofenozide, hexaflumuron, hydramethylnon, imidacloprid, isofenphos, indoxacarb, isoprocarb, isoxathion, lepimectin, lufenuron, malathion, meperfluthrin, metaflumizone, metaldehyde, methamidophos, methidathion, methacrifos, metaflumizone, metalcarb, methomyl, methoprene, methoxychlor, methoxyfenozide, methyl bromide, monocrotophos, muscalure, nitenpyram, novaluron, noviflumuron, omethoate, oxamyl, oxydemeton-methyl, oxydeprofos, parathion, parathion-methyl, pentachlorophenol (PCP), permethrin, phenothrin, phenthoate, phoxim, phorate, phosalone, phosmet, phosphamidon, pirimicarb, pirimiphos-methyl, profenofos, prothiofos, propaphos, protrifenbute, pymetrozine, pyraclofos, pyrethrins, pyridalyl, pyrifluquinazon, pyriprole, pyrafluprole, pyriproxyfen, resmethrin, rotenone, SI-0405 (test name), sulprofos, silafluofen, spinetoram, spinosad, spirotetramat, sulfoxaflor, sulfotep, SYJ-159 (test name), tebfenozide, teflubenzuron, tefluthorin, terbufos, tetrachlorvinphos, tetramethrin, d-tetramethrin, tetramethylfluthrin, thiacloprid, thiocyclam, thiodicarb, thiamethoxam, thiofanox, thiometon, tolfenpyrad, tralomethrin, trichlorfon, triazuron, triflumuron, vamidothion, ME-5343 (test name), and the like.

If desired, a surfactant can be added to the composition of the present invention. Examples of the surfactant will be listed in (A), (B), (C), (D), and (E) below.

(A) Nonionic Surfactants:

(A-1) Polyethylene glycol surfactants: for example, a polyoxyethylene alkyl (for example $C_{8-18}$) ether, an ethylene oxide adduct of alkyl naphthol, a polyoxyethylene (mono or di) alkyl (for example $C_{8-12}$) phenyl ether, a formalin condensate of a polyoxyethylene (mono or di) alkyl (for example $C_{8-12}$) phenyl ether, a polyoxyethylene (mono, di, or tri) phenyl phenyl ether, a polyoxyethylene (mono, di, or tri) benzyl phenyl ether, a polyoxypropylene (mono, di, or tri) benzyl phenyl ether, a polyoxyethylene (mono, di, or tri) styryl phenyl ether, a polyoxypropylene (mono, di, or tri) styryl phenyl ether, a polymer of polyoxyethylene (mono, di, or tri) styryl phenyl ether, a polyoxyethylene polyoxypropylene (mono, di, or tri) styryl phenyl ether, a polyoxyethylene polyoxypropylene block polymer, an alkyl (for example $C_{8-18}$) polyoxyethylene polyoxypropylene block polymer ether, an alkyl (for example $C_{8-12}$) phenyl polyoxyethylene polyoxypropylene block polymer ether, a polyoxyethylene bisphenyl ether, a polyoxyethylene resin acid ester, a polyoxyethylene fatty acid (for example $C_{8-18}$) monoester, a polyoxyethylene fatty acid (for example $C_{8-18}$) diester, a polyoxyethylene sorbitan (mono, di, or tri) fatty acid (for example $C_{8-18}$) ester, a glycerol fatty acid ester ethylene oxide adduct, a castor oil ethylene oxide adduct, a hydrogenated castor oil ethylene oxide adduct, an alkyl (for example $C_{8-18}$) amine ethylene oxide adduct, and a fatty acid (for example $C_{8-18}$) amide ethylene oxide adduct.

(A-2) Polyhydric alcohol surfactants: for example, a glycerol fatty acid ester, a polyglycerol fatty acid ester, a pentaerythritol fatty acid ester, a sorbitol fatty acid (for example $C_{8-18}$) ester, a sorbitan (mono, di, or tri) fatty acid (for example $C_{8-18}$) ester, a sucrose fatty acid ester, a polyhydric alcohol alkyl ether, an alkyl glycoside, an alkyl polyglycoside, and a fatty acid alkanol amide.

(A-3) Acetylene surfactants: for example, acetylene glycol, acetylene alcohol, an ethylene oxide adduct of acetylene glycol, and an ethylene oxide adduct of acetylene alcohol.

(B) Anionic Surfactants:

(B-1) Carboxylic acid surfactants: for example, a carboxylic acid, such as poly acrylic acid, poly methacrylic acid, poly maleic acid, poly maleic anhydride, a copolymer of maleic acid or maleic anhydride and an olefin (for example, isobutylene, diisobutylene, and the like), a copolymer of acrylic acid and itaconic acid, a copolymer of methacrylic acid and itaconic acid, a copolymer of maleic acid or maleic anhydride and styrene, a copolymer of acrylic acid and methacrylic acid, a copolymer of acrylic acid and methyl acrylate ester, a copolymer of acrylic acid and vinyl acetate, a copolymer of acrylic acid and maleic acid or maleic anhydride, a polyoxyethylene alkyl (for example $C_{8-18}$) ether acetic acid, an N-methyl-fatty acid (for example $C_{8-18}$) sarcosinate, a resin acid, and a fatty acid (for example $C_{8-18}$); and salts of these carboxylic acids.

(B-2) Sulfuric acid ester surfactants: for example, a sulfuric acid ester, such as an alkyl (for example $C_{8-18}$) sulfuric acid ester, a polyoxyethylene alkyl (for example $C_{8-18}$) ether sulfuric ester, a polyoxyethylene (mono or di) alkyl (for example $C_{8-12}$) phenyl ether sulfuric acid ester, a sulfuric acid ester of a polymer of a polyoxyethylene (mono or di) alkyl (for example $C_{8-12}$) phenyl ether, a polyoxyethylene (mono, di, or tri) phenyl phenyl ether sulfuric acid ester, a polyoxyethylene (mono, di, or tri) benzyl phenyl ether sulfuric acid ester, a polyoxyethylene (mono, di, or tri) styryl phenyl ether sulfuric acid ester, a sulfuric acid ester of a polymer of a polyoxyethylene (mono, di, or tri) styryl phenyl ether, a sulfuric acid ester of a polyoxyethylene polyoxypropylene block polymer, a sulfated oil, a sulfated fatty acid ester, a sulfated fatty acid, and a sulfated olefin; and salts of these sulfuric acid esters.

(B-3) Sulfonic acid surfactants: for example, a sulfonic acid, such as a paraffin (for example $C_{8-22}$) sulfonic acid, an alkyl (for example $C_{8-12}$) benzene sulfonic acid, a formalin condensate of an alkyl (for example $C_{8-12}$) benzene sulfonic acid, a formalin condensate of a cresol sulfonic acid, an α-olefin (for example $C_{8-16}$) sulfonic acid, a dialkyl (for example $C_{8-12}$) sulfo succinic acid, a lignin sulfonic acid, a polyoxyethylene (mono or di) alkyl (for example $C_{8-12}$) phenyl ether sulfonic acid, a polyoxyethylene alkyl (for example $C_{8-18}$) ether sulfo succinic acid half ester, a naphthalene sulfonic acid, a (mono or di) alkyl (for example $C_{1-6}$) naphthalene sulfonic acid, a formalin condensate of a naphthalene sulfonic acid, a formalin condensate of a (mono or di) alkyl (for example $C_{1-6}$) naphthalene sulfonic acid, a formalin condensate of a creosote oil sulfonic acid, an alkyl (for example $C_{8-12}$) diphenyl ether disulfonic acid, Igepon T (product name), a polystyrene sulfonic acid, and a copolymer of a styrene sulfonic acid and methacrylic acid; and salts of these sulfonic acids.

(B-4) Phosphoric acid ester surfactants: for example, a phosphoric acid ester, such as an alkyl (for example $C_{8-12}$) phosphoric acid ester, a polyoxyethylene alkyl (for example $C_{8-18}$) ether phosphoric acid ester, a polyoxyethylene (mono or di) alkyl (for example $C_{8-12}$) phenyl ether phosphoric acid ester, a phosphoric acid ester of a polymer of a polyoxyethylene (mono, di, or tri) alkyl (for example $C_{8-12}$) phenyl ether, a polyoxyethylene (mono, di, or tri) phenyl phenyl ether phosphoric acid ester, a polyoxyethylene (mono, di, or tri) benzyl phenyl ether phosphoric acid ester, a polyoxyethylene (mono, di, or tri) styryl phenyl ether phosphoric acid ester, a phosphoric acid ester of a polymer of a polyoxyethylene (mono, di, or tri) styryl phenyl ether, a phosphoric acid ester of a polyoxyethylene polyoxypropylene block polymer, phosphatidylcholine, phosphatidyl ethanolimine, and a condensed phosphoric acid (for example, tripoly phosphoric acid); and salts of these phosphoric acid esters.

Examples of counter ions for salts in (B-1) to (B-4) of above include alkaline metals (lithium, sodium, potassium, and the like), alkaline earth metals (calcium, magnesium, and the like), ammonium, and a variety of amines (for example, an alkylamine, a cycloalkylamine, and an alkanol amine).

(C) Cationic Surfactants:

For example, an alkylamine, an alkyl quaternary ammonium salt, an ethylene oxide adduct of an alkylamine, and an ethylene oxide adduct of an alkyl quaternary ammonium salt.

(D) Amphoteric Surfactants:

(D-1) Betaine surfactants: for example, an alkyl (for example $C_{8-18}$) dimethylamino acetic acid betaine, an acyl (for example $C_{8-18}$) aminopropyldimethylamino acetic acid betaine, an alkyl (for example $C_{8-18}$) hydroxysulfo betaine, and a 2-alkyl (for example $C_{8-18}$)—N-carboxymethyl-N-hydroxyethyl imidazolinium betaine.

(D-2) Amino acid surfactants: for example, an alkyl (for example $C_{8-18}$) amino propionic acid, an alkyl (for example $C_{8-18}$) amino dipropionic acid, and an N-acyl (for example $C_{8-18}$)—N'-carboxyethyl-M-hydroxyethyl ethylenediamine.

(D-3) Amine oxide surfactants: for example, an alkyl (for example $C_{8-18}$) dimethylamine oxide, and an acyl (for example $C_{8-18}$) aminopropyl dimethylamine oxide.

(E) Other Surfactants:

(E-1) Silicon surfactants: for example, a polyoxyethylene-methyl polysiloxane copolymer, a polyoxypropylene-methyl polysiloxane copolymer, and a poly(oxyethylene-oxypropylene)-methyl polysiloxane copolymer.

(E-2) Fluorine surfactants: for example, a perfluoro alkenyl benzenesulfonate, a perfluoro alkyl sulfonate, a perfluoro alkyl carboxylate, a perfluoro alkenyl polyoxyethylene ether, a perfluoro alkyl polyoxyethylene ether, and a perfluoro alkyl trimethyl ammonium salt.

These surfactants can be used alone, or two or more of them can be used in a mixed state, and can be mixed in any ratio. Although the content of the surfactant in the composition of the present invention can suitably be selected, the content is preferably within a range of 0.1 to 20 parts by weight, provided that the composition of the present invention is 100 parts by weight.

The composition of the present invention can further contain a variety of auxiliary agents. The auxiliary agents that can be used are a thickener, an organic solvent, an antifreezing agent, an antifoaming agent, an anti-bacterial/fungal agent, a colorant, and the like, and specific examples thereof will be listed below.

The thickener is not particularly limited, and organic or inorganic substances, which are natural, synthetic, or semi-synthetic, can be used. Specific examples thereof include heteropolysaccharides, such as xanthan gum, welan gum, and rhamsan gum; water-soluble macromolecule compounds, such as polyvinyl alcohol, polyvinyl pyrrolidone, polyacrylic acid, sodium polyacrylate, and polyacrylamide; cellulose derivatives, such as methyl cellulose, carboxymethyl cellulose, carboxyethyl cellulose, hydroxyethyl cellulose, and hydroxypropyl cellulose; and smectite clay minerals, such as montmorillonite, saponite, hectorite, bentonite, Laponite, and synthetic smectite. These thickeners can be used alone, or two or more of them can be used in a mixed state and can be mixed in any ratio. These thickeners can be added directly, or can be added after dispersing them in water. As a content of the thickener in the composition of the present invention, any amount can be used.

Examples of the organic solvent include alcohols, such as ethylene glycol, diethylene glycol, propylene glycol, dipropylene glycol, and isopropanol; ethers, such as butyl cellosolve; ketones, such as cyclohexanone; esters, such as γ-butyrolactone; acid amides, such as N-methyl pyrrolidone and N-octyl pyrrolidone; aromatic hydrocarbons, such as xylene, an alkyl benzene, a phenylxylyl ethane, and an alkyl naphthalene; aliphatic hydrocarbons, such as a machine oil, normal paraffin, isoparaffin, and naphthene; a mixture of an aromatic hydrocarbon and an aliphatic hydrocarbon, such as kerosene; and fats and oils, such as soybean oil, flaxseed oil, canola oil, coconut oil, cottonseed oil, and castor oil.

As the antifreezing agent, for example, ethylene glycol, diethylene glycol, propylene glycol, or glycerin can be used. Among them, propylene glycol and glycerin are preferable. As a content of the antifreezing agent in the composition of the present invention, any amount can be used.

An antifoaming agent such as silicone emulsion, an anti-bacterial/fungal agent, a colorant, and the like may further be blended in the composition of the present invention.

Although the method for manufacturing the composition of the present invention is not particularly limited, the method includes adding the aforementioned ingredients in a dispersion medium, and mixing them with a mixer to obtain the composition. If necessary, each of agrichemical ingredients, surfactants, and other auxiliary agents may be pulverized in a dry or wet pulverizer individually, or as a mixture thereof.

Dry pulverization can be conducted by using a hammer mill, a pin mill, a jet mill, a ball mill, a roll mill, or the like. Wet pulverization can be conducted by using a wet pulverizer, such as an inline mill and a bead mill.

For example, the composition of the present invention can be applied to crops, trees, or soil where they grow, by spraying the composition as straight or as diluted with water approximately 50 to 5,000 times, by using a sprayer or the like; or by spraying the composition as straight or as diluted with water approximately 2 to 100 times, by using a helicopter or the like from the air.

EXAMPLES

Hereinafter, the present invention will be explained in further detail according to the examples below; however, the present invention is not limited to these examples.

Reference Example

Manufacturing of (S)-Compound A

The racemate 4-(5-(3,5-dichlorophenyl)-5-trifluoromethyl-4,5-dihydroisoxazol-3-yl)-2-methyl benzoic acid can be synthesized according to the method described in Patent Document 1 or Patent Document 4, and can be used as a starting material.

(S)-4-(5-(3,5-dichlorophenyl)-5-trifluoromethyl-4,5-dihydroisoxazol-3-yl)-2-methyl benzoic acid can be synthesized from the racemate 4-(5-(3,5-dichlorophenyl)-5-trifluoromethyl-4,5-dihydroisoxazol-3-yl)-2-methyl benzoic acid, according to the method described in Patent Document 3.

The (S)-Compound A can be synthesized from (S)-4-(5-(3,5-dichlorophenyl)-5-trifluoromethyl-4,5-dihydroisoxazol-3-yl)-2-methyl benzoic acid, according to the method described in Patent Document 1 or Patent Document 4.

The (S)-Compound A obtained according to the manufacturing method was purified by using a preparative liquid chromatography system equipped with a chiral column to obtain 250 mg of the (S)-Compound A having an optical purity of 99% ee or above. The property of the obtained (S)-Compound A was amorphous.

The conditions of the preparative liquid chromatography system equipped with a chiral column described above will be shown below.

Column: CHIRALPAK (registered trademark) AD-H 2.0 cmφ×25 cm

Guard column: CHIRALPAK (registered trademark) AD-H 1.0 cmφ×2 cm (manufactured by Daicel Corporation)

Oven temperature: 40° C.

UV detector: 254 nm

Eluant: n-hexane/ethanol=50/50 (volume ratio)

Flow velocity: 5.0 ml/minute

Injection volume: To 100 mg of the (S)-Compound A, 1.0 ml of ethanol was added to dissolve the compound therein, and then 1.0 ml of n-hexane was added, and 500 μl of the resultant solution was used for 1 cycle.

1 cycle: 24 minutes

When the obtained (S)-Compound A was analyzed by high performance liquid chromatography (hereinafter, abbreviated as HPLC), only the peak corresponding to the (S)-Compound A was detected, and the peak corresponding to the (R)-Compound A was not detected.

Further, how the absolute configuration of the Compound A was identified will be explained below. According to the method described in Patent Document 3, a single crystal X-ray structural analysis was conducted for the diastereomeric salt of the (S)-4-(5-(3,5-dichlorophenyl)-5-trifluoromethyl-4,5-dihydroisoxazol-3-yl)-2-methyl benzoic acid and (−)-1-phenylethyl amine, and the absolute configuration of the (S)-4-(5-(3,5-dichlorophenyl)-5-trifluoromethyl-4,5-dihydroisoxazol-3-yl)-2-methyl benzoic acid was identified as "S." The (S)-Compound A was synthesized from the crystal of above according to the method described in Patent Document 1, Patent Document 3, Patent Document 4, and the like, and was used as the standard substance. Both of the retention times of the (S)-Compound A obtained in Reference Example 1 and the (S)-Compound A as the standard substance, which were analyzed by high performance liquid chromatography (hereinafter, abbreviated as HPLC), were 19.4 minutes. Based on the result above, the absolute configuration of the Compound A obtained in Reference Example 1 was confirmed as "S."

The analytical conditions of the HPLC described above (hereinafter, called "the analytical conditions of the optically active substance") will be shown below.

Column: CHIRALPAK (registered trademark) AD-H 5 μm, 4.6×250 mm (manufactured by Daicel Corporation)
Oven temperature: 40° C.
UV detector: 254 nm
Eluant: n-hexane/ethanol=80/20 (volume ratio)
Flow velocity: 1.0 ml/minute
Injection volume: 10 μl Example 1

Manufacture of Crystalline Polymorph of (S)-Compound A (Toluene Solvent)

Example 1-1

20 μL of toluene was added to 50 mg of the (S)-Compound A, which was obtained in the Reference Example, at 20° C., and it was confirmed that the (S)-Compound A was completely dissolved in toluene. After that, the solution was rested in an open system for several hours, and precipitation of a needle crystal was confirmed. Crystal growth was continued at 20° C., and a quantitative amount of the needle crystal was obtained one week later. The obtained needle crystal had peaks at angles of diffraction (2θ) of 3.66, 5.73, 6.56, 7.38, 7.76, 9.18, 11.52, 12.24, 12.92, 13.19, 13.98, 14.81, 15.60, 16.04, 16.36, 16.98, 17.59, 18.02, 18.27, 18.47, 18.87, 19.45, 20.21, 20.48, 20.62, 21.12, 21.51, 21.92, 22.20, 22.66, 23.19, 23.58, 24.24, 24.59, 24.96, 25.12, 25.74, 26.08, 26.48, 27.52, 28.20, 29.18, 29.61, 30.06, 30.50, 30.88, 35.77, and 38.92 in a powder X-ray diffraction spectrum. The obtained chart of the powder X-ray diffraction is shown in FIG. 1. In an HPLC analysis under the analytical conditions of the optically active substance, only the peak corresponding to the S-isomer was detected, and the peak corresponding to the R form was not detected.

Example 1-2

Figure 2:
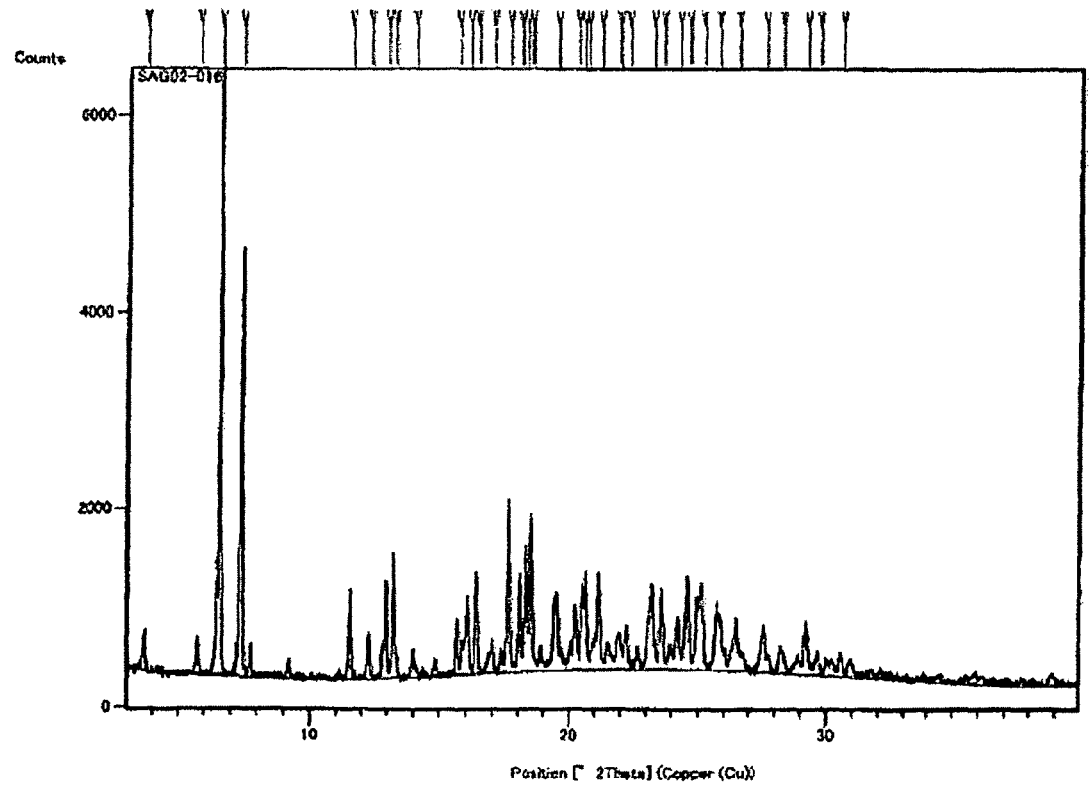
FIG. 2 is a chart of powder X-ray diffraction for the crystalline polymorph of the (S)-Compound A obtained in Example 1-2.

20 μL of toluene was added to 50 mg of the (S)-Compound A (amorphous of 98% ee), which was obtained according to the method of Reference Example, at 20° C., and it was confirmed that the (S)-Compound A was completely dissolved in toluene. After that, the solution was rested in an open system for several hours, and precipitation of a needle crystal was confirmed. Crystal growth was continued at 20° C., and a quantitative amount of the needle crystal was obtained one week later. The obtained needle crystal was measured by powder X-ray diffraction, and peaks were obtained at the angles of diffraction (2θ) of 3.66, 5.73, 6.57, 7.38, 11.52, 12.24, 12.93, 13.20, 13.99, 15.61, 16.05, 16.37, 16.96, 17.60, 18.03, 18.28, 18.47, 19.45, 20.22, 20.47, 20.64, 21.13, 21.88, 22.23, 23.19, 23.58, 24.20, 24.58, 25.13, 25.72, 26.48, 27.55, 28.17, 29.16, 29.63, and 30.52. The obtained chart of the powder X-ray diffraction is shown in FIG. 2. In an HPLC analysis under the analytical conditions of the optically active substance, an area ratio of the peak corresponding to the (S)-Compound A/the peak corresponding to the R form of Compound A was 99.1/0.9.

Example 1-3

Figure 3:
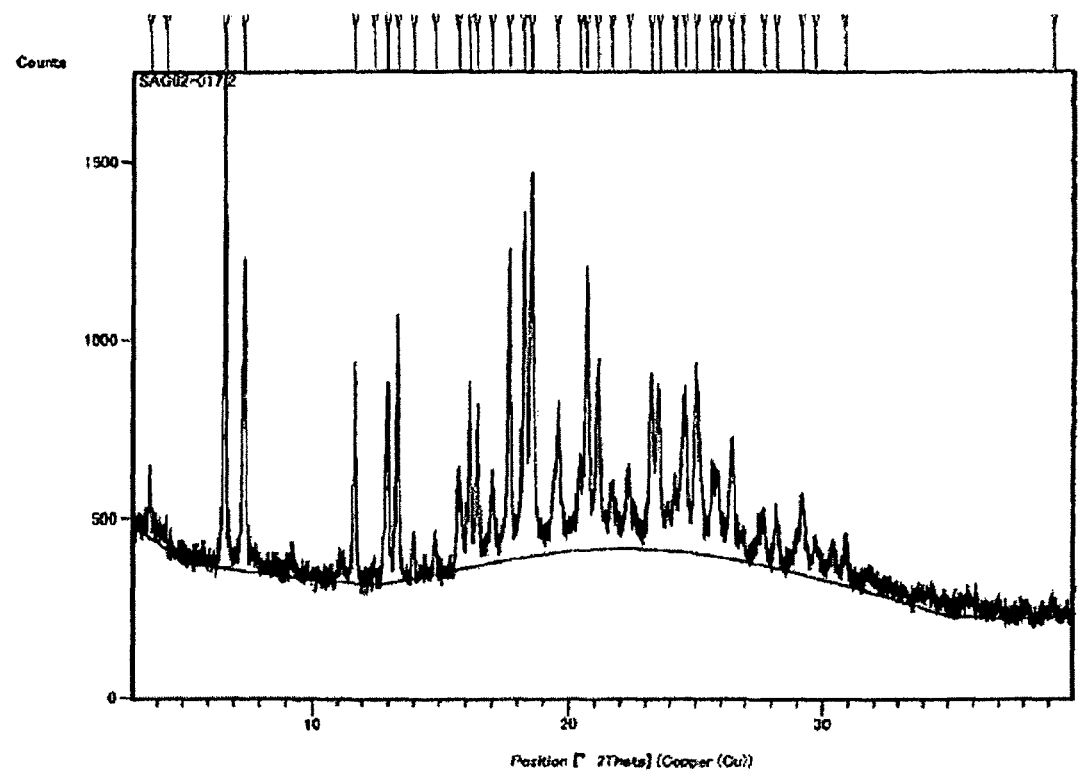
FIG. 3 is a chart of powder X-ray diffraction for the crystalline polymorph of the (S)-Compound A obtained in Example 1-3.

20 μL of toluene was added to 50 mg of the (S)-Compound A (amorphous of 98% ee), which was obtained according to the method of Reference Example, at 20° C., and it was confirmed that the (S)-Compound A was completely dissolved in toluene. After that, the solution was rested in an open system for several hours, and precipitation of a needle crystal was confirmed. Crystal growth was continued at 20° C., and a quantitative amount of the needle crystal was obtained one week later. The obtained needle crystal was subjected to drying in vacuo three times, two hours for each time, thus for six hours in total, under the conditions of 50° C., 10 mmHg. The obtained crystal was measured by powder X-ray diffraction, and peaks were obtained at the angles of diffraction (2θ) of 3.67, 4.30, 6.63, 7.37, 11.66, 12.40, 12.93, 13.32, 13.96, 14.78, 15.69, 16.12, 16.43, 16.98, 17.65, 18.24, 18.52, 19.51, 20.39, 20.65, 21.08, 21.65, 22.34, 23.22, 23.54, 24.16, 24.54, 25.00, 25.61, 25.85, 26.39, 26.83, 27.64, 28.16, 29.17, 29.67, 30.82, and 39.16. The obtained chart of the powder X-ray diffraction is shown in FIG. 3. In an HPLC analysis under the analytical conditions of the optically active substance, an area ratio of the peak corresponding to the (S)-Compound A/the peak corresponding to the R form of Compound A was 98.7/1.3.

Example 2

Manufacture of Crystalline Polymorph of (S)-Compound A by Using Seed Crystal (Toluene Solvent)

Figure 4:
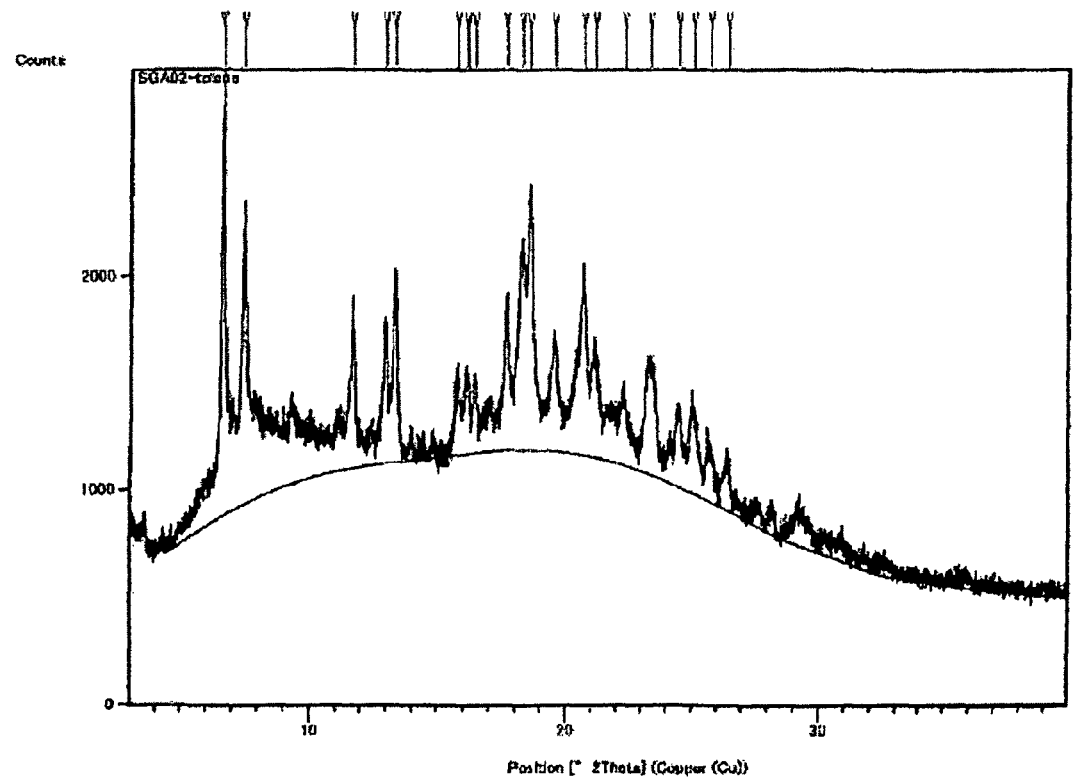
FIG. 4 is a chart of powder X-ray diffraction for the crystalline polymorph of the (S)-Compound A obtained in Example 2.

400 μL of toluene was added to 401.6 mg of the (S)-Compound A (amorphous of 98% ee), which was obtained according to the method of Reference Example, at 20° C., and it was confirmed that the (S)-Compound A was completely dissolved in toluene. After that, a trace amount of the crystal of the (S)-Compound A obtained in Example 1-1 was added to the toluene solution as the seed crystal. After the addition of the seed crystal, the toluene solution was rested at 4° C., and precipitation and increase of the crystal was confirmed 2 days later. The obtained crystal was subjected to drying in vacuo for 14 hours in total, under the condition of 40 to 45° C., 16 to 20 mmHg, and then 401.6 mg of the crystal was obtained. The obtained crystal was measured by powder X-ray diffraction, and peaks were obtained at the angles of diffraction (2θ) of 6.64, 7.43, 11.65, 12.91, 13.30, 15.72, 16.08, 16.39, 17.64, 18.22, 18.54, 19.50, 20.65, 21.10, 22.27, 23.32, 24.45, 25.00, 25.70, and 26.38. The obtained chart of the powder X-ray diffraction is shown in FIG. 4. In an HPLC analysis under the analytical conditions of the optically active substance, an area ratio of the peak corresponding to the (S)-Compound A/the peak corresponding to the R form of Compound A was 98.7/1.3.

Example 3

Manufacture of Crystalline Polymorph of (S)-Compound A (Ethanol Solvent)

15 μL of ethanol was added to 50 mg of the (S)-Compound A, which was obtained in the Reference Example, at 20° C., and it was confirmed that the (S)-Compound A was completely dissolved in ethanol. After that, the ethanol solution was rested for forty days to precipitate a crystal. The obtained crystal was measured by powder X-ray diffraction, and peaks were obtained at the angles of diffraction (2θ) of 3.46, 4.48, 7.12, 8.69, 8.92, 10.50, 11.07, 11.94, 12.49, 12.94, 14.49, 15.22, 15.62, 16.26, 16.64, 17.27, 17.96, 19.20, 20.04, 20.62, 21.08, 22.36, 22.68, 23.02, 23.82, 24.96, 25.65, 26.46, 27.09, 27.67, 28.57, 29.18, 30.01, 30.78, 31.34, 32.14, 33.79, 35.85, and 37.57. The obtained chart of the powder X-ray diffraction is shown in FIG. 5. In an HPLC analysis under the analytical conditions of the optically active substance, only the peak corresponding to the (S)-Compound A was detected, and the peak corresponding to the R form of the Compound A was not detected.

INDUSTRIAL APPLICABILITY

According to the present invention, a crystal of the optically active substance of the Compound A can be manufactured.

The invention claimed is:
1. A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=6.56, 7.38, 11.52, 12.92, 13.19, 15.60, 16.04, 16.36, 17.59, 18.27, 18.47, 19.45, 20.62, 21.12, 22.20, 23.19, 24.59, 25.12, 25.74, and 26.48 in powder X-ray diffraction with a Cu—Kα ray.

2. The crystalline polymorph according to claim 1, wherein characteristic peaks are at angles of diffraction 2θ=3.66, 5.73, 6.56, 7.38, 7.76, 9.18, 11.52, 12.24, 12.92, 13.19, 13.98, 14.81, 15.60, 16.04, 16.36, 16.98, 17.59, 18.02, 18.27, 18.47, 18.87, 19.45, 20.21, 20.48, 20.62, 21.12, 21.51, 21.92, 22.20, 22.66, 23.19, 23.58, 24.24, 24.59, 24.96, 25.12, 25.74, 26.08, 26.48, 27.52, 28.20, 29.18, 29.61, 30.06, 30.50, 30.88, 35.77, and 38.92 in powder X-ray diffraction with a Cu—Kα ray.

3. A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=6.56±0.2, 7.38±0.2, 11.52±0.2, 12.92±0.2, 13.19±0.2, 15.60±0.2, 16.04±0.2, 16.36±0.2, 17.59±0.2, 18.27±0.2, 18.47±0.2, 19.45±0.2, 20.62±0.2, 21.12±0.2, 22.20±0.2, 23.19±0.2, 24.59±0.2, 25.12±0.2, 25.74±0.2, and 26.48±0.2 in powder X-ray diffraction with a Cu—Kα ray.

4. The crystalline polymorph according to claim 3, wherein characteristic peaks are at angles of diffraction 2θ=3.66±0.2, 5.73±0.2, 6.56±0.2, 7.38±0.2, 7.76±0.2, 9.18±0.2, 11.52±0.2, 12.24±0.2, 12.92±0.2, 13.19±0.2, 13.98±0.2, 14.81±0.2, 15.60±0.2, 16.04±0.2, 16.36±0.2, 16.98±0.2, 17.59±0.2, 18.02±0.2, 18.27±0.2, 18.47±0.2, 18.87±0.2, 19.45±0.2, 20.21±0.2, 20.48±0.2, 20.62±0.2, 21.12±0.2, 21.51±0.2, 21.92±0.2, 22.20±0.2, 22.66±0.2, 23.19±0.2, 23.58±0.2, 24.24±0.2, 24.59±0.2, 24.96±0.2, 25.12±0.2, 25.74±0.2, 26.08±0.2, 26.48±0.2, 27.52±0.2, 28.20±0.2, 29.18±0.2, 29.61±0.2, 30.06±0.2, 30.50±0.2, 30.88±0.2, 35.77±0.2, and 38.92±0.2 in powder X-ray diffraction with a Cu—Kα ray.

5. The crystalline polymorph according to claim 1, wherein a diffraction curve of the crystalline polymorph is substantially identical to a diffraction curve shown in FIG. 1 of the present application in powder X-ray diffraction with a Cu—Kα ray.

6. The crystalline polymorph according to claim 1, wherein the crystalline polymorph is obtained by dissolving (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide in toluene, and then precipitating a crystal.

7. A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=3.46, 4.48, 7.12, 8.69, 8.92, 10.50, 11.07, 11.94, 12.49, 12.94, 14.49, 15.22, 15.62, 16.26, 16.64, 17.27, 17.96, 19.20, 20.04, 20.62, 21.08, 22.36, 22.68, 23.02, 23.82, 24.96, 25.65, 26.46, 27.09, 27.67, 28.57, 29.18, 30.01, 30.78, 31.34, 32.14, 33.79, 35.85, and 37.57 in powder X-ray diffraction with a Cu—Kα ray.

8. A crystalline polymorph of (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide that has characteristic peaks at angles of diffraction 2θ=3.46±0.2, 4.48±0.2, 7.12±0.2, 8.69±0.2, 8.92±0.2, 10.50±0.2, 11.07±0.2, 11.94±0.2, 12.49±0.2, 12.94±0.2, 14.49±0.2, 15.22±0.2, 15.62±0.2, 16.26±0.2, 16.64±0.2, 17.27±0.2, 17.96±0.2, 19.20±0.2, 20.04±0.2, 20.62±0.2, 21.08±0.2, 22.36±0.2, 22.68±0.2, 23.02±0.2, 23.82±0.2, 24.96±0.2, 25.65±0.2, 26.46±0.2, 27.09±0.2, 27.67±0.2, 28.57±0.2, 29.18±0.2, 30.01±0.2, 30.78±0.2, 31.34±0.2, 32.14±0.2, 33.79±0.2, 35.85±0.2, and 37.57±0.2 in powder X-ray diffraction with a Cu—Kα ray.

9. The crystalline polymorph according to claim 7, wherein a diffraction curve of the crystalline polymorph is substantially identical to a diffraction curve shown in FIG. 5 of the present application in powder X-ray diffraction with a Cu—Kα ray.

10. The crystalline polymorph according to claim 7, wherein
the crystalline polymorph is obtained by dissolving (S)-4-[5-(3,5-dichlorophenyl)-5-(trifluoromethyl)-4,5-dihydroisoxazol-3-yl]-2-methyl-N-[2-oxo-2-(2,2,2-trifluoroethylamino)ethyl]benzamide in ethanol, and then precipitating a crystal.

11. A composition for pest control, comprising:
the crystalline polymorph as claimed in claim 1.

12. A composition for pest control, comprising:
the crystalline polymorph as claimed in claim 7.

* * * * *